US009788914B2

(12) United States Patent
Dhanasingh et al.

(10) Patent No.: US 9,788,914 B2
(45) Date of Patent: Oct. 17, 2017

(54) TEMPLATE FOR BILATERAL SYMMETRIC STIMULATOR FIXATION/IMPLANTATION

(71) Applicant: MED-EL Elektromedizinische Geraete GmbH, Innsbruck (AT)

(72) Inventors: Anandhan Dhanasingh, Innsbruck (AT); Claude Jolly, Innsbruck (AT); Andreas Harnisch, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 151 days.

(21) Appl. No.: 14/874,537

(22) Filed: Oct. 5, 2015

(65) Prior Publication Data

US 2016/0096019 A1    Apr. 7, 2016

Related U.S. Application Data

(60) Provisional application No. 62/060,042, filed on Oct. 6, 2014.

(51) Int. Cl.
| | | |
|---|---|---|
| *A61N 1/00* | (2006.01) | |
| *A61B 90/11* | (2016.01) | |
| *A61N 1/05* | (2006.01) | |
| *A61B 17/00* | (2006.01) | |

(Continued)

(52) U.S. Cl.
CPC ..... *A61B 90/11* (2016.02); *A61B 2017/00787* (2013.01); *A61B 2017/568* (2013.01); *A61N 1/0541* (2013.01); *H04R 25/606* (2013.01); *H04R 2225/67* (2013.01); *H04R 2460/13* (2013.01)

(58) Field of Classification Search
CPC ... A61N 1/0541; A61N 1/36032; A61N 1/375
USPC ....................................................... 607/137
See application file for complete search history.

(56) References Cited

U.S. PATENT DOCUMENTS

| | | | |
|---|---|---|---|
| 2003/0199886 A1* | 10/2003 | Thomas | A61B 90/11 606/130 |
| 2008/0262468 A1 | 10/2008 | Clifford et al. | |
| 2012/0179187 A1 | 7/2012 | Loushin et al. | |

(Continued)

FOREIGN PATENT DOCUMENTS

| | | | | |
|---|---|---|---|---|
| AU | WO 2009132389 A1 * | 11/2009 | ............. | A61B 90/06 |
| WO | WO 2009132389 | 11/2009 | | |

OTHER PUBLICATIONS

International Searching Authority, Authorized Officer Blaine R. Copenheaver, International Search Report and Written Opinion, PCT/US2015/053916, dated Dec. 28, 2015, 13 pages.

*Primary Examiner* — Amanda Patton
*Assistant Examiner* — Philip C Edwards
(74) *Attorney, Agent, or Firm* — Sunstein Kann Murphy & Timbers LLP

(57) ABSTRACT

A bilateral hearing implant surgical template arrangement is described. An adjustable headpiece with left and right sides fits over the head of a surgical patient. There are left and right implant stimulator templates, each configured to conform against an underlying side of the patient's head and each connected to a corresponding left and right side of the adjustable headpiece by an adjustable connection. Each adjustable connection is configured to allow adjustment of the position of the implant stimulator template with respect to the adjustable headpiece so as to define stimulator implantation sites at symmetric locations on each side of the patient's head.

9 Claims, 4 Drawing Sheets

(51) Int. Cl.
 A61B 17/56 (2006.01)
 H04R 25/00 (2006.01)

(56) References Cited

U.S. PATENT DOCUMENTS

2013/0041381 A1 2/2013 Clair
2014/0107400 A1 4/2014 Busca Grisoni et al.

* cited by examiner

TEMPLATE FOR BILATERAL SYMMETRIC STIMULATOR FIXATION/IMPLANTATION

This application claims priority from U.S. Provisional Patent Application 62/060,042, filed Oct. 6, 2014, which is incorporated herein by reference in its entirety.

FIELD OF THE INVENTION

The present invention relates to hearing implant systems, and more specifically to surgical templates for implantation of bilateral hearing implant systems.

BACKGROUND ART

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus hearing implant systems include brainstem implants, middle brain implants, etc. each stimulating a specific auditory target in the hearing system.

FIG. 1 also shows some components of a typical cochlear implant system where an external microphone provides an audio signal input to an external behind the ear (BTE) processor 111 in which various signal processing schemes can be implemented. The processed signal is then converted into a digital data format for transmission by external transmitter coil 107 into the implant stimulator 108. Besides receiving the processed audio information, the implant stimulator 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective electrical stimulation of the cochlea 104.

Bilateral cochlear implant systems provide cochlear implants to both the left and right ears. Normally two sequential implantation surgeries are performed. The first surgery is performed on one side, and the second surgery is then performed some time later, sometimes years after the first implantation surgery, and even different surgeons may perform the separate surgeries. During the first implantation surgery, no data is documented on the exact position (e.g. regarding implantation angle) that can be used for the second side.

During both surgeries, the fixation position of implant stimulator is very important. The length of the connecting cable from the BTE processor to the external transmitter coil very much depends on the position of the implant stimulator. And in a bilateral implant system with a single external processor, the sound received by the processor from both sides should be symmetrical, otherwise there could be undesired inter aural time differences.

SUMMARY OF THE INVENTION

Embodiments of the present invention are directed to surgical template arrangements for a bilateral hearing implant system. An adjustable headpiece with left and right sides is configured to fit over the head of a surgical patient. There are left and right implant stimulator templates, each connected to a corresponding left and right side of the adjustable headpiece by an adjustable connection and configured to conform against an underlying side of the patient's head. Each implant stimulator template has an implant outline defining an area corresponding to an implanted stimulator of the bilateral hearing implant system. Each adjustable connection is configured to allow adjustment of the position of the implant stimulator template with respect to the adjustable headpiece so as to define stimulator implantation sites at symmetric locations on each side of the patient's head.

Each adjustable connection may be configured to enable the corresponding implant stimulator template to adjustably pivot through an adjustment angle with respect to the adjustable headpiece. Specifically, each adjustable connection may be configured to allow adjustable pivoting through a limited range of recommended adjustment angles. And/or there may be an angle indicator scale configured to provide a visual indication of the adjustment angle and/or a holding magnet located within the outer outline of one of the implant stimulator templates configured to hold that implant stimulator template securely on the skin over an implanted magnet of a previously implanted stimulator to allow determination of the adjustment angle.

Each implant stimulator template may include marking openings configured for location marking on the underlying tissue during implantation surgery. At least one template may be made of malleable plate metal and/or at least one template may be made of resilient polymer material.

In some embodiments, there may also be at least one behind the ear (BTE) processor template located on the adjustable headpiece at one of the adjustable connections. The at least one BTE processor template has a processor outline defining an area corresponding to an external BTE processor device of the bilateral hearing implant system, and the at least one BTE processor template is configured to fit behind the ear pinna of the recipient patient in a post-surgical operational position and conform against an underlying side of the patient's head. In some embodiments, there may be a pair of left and right side BTE templates, one on each side of the adjustable headpiece at the adjustable connection for the corresponding left and right side implant stimulator templates.

Embodiments of the present invention also include surgical template arrangements for a bilateral hearing implant system without an adjustable headpiece. An implant stimulator template is configured to fit behind an outer ear pinna of a recipient patient at an adjustable connection and is configured to conform against an underlying side of the head. The implant stimulator template has an implant outline defining an area corresponding to an implanted stimulator of the bilateral hearing implant system. The adjustable connection is configured to allow adjustment of the position of the implant stimulator template with respect to the outer ear pinna so as to define stimulator implantation sites at symmetric locations on each side of the patient's head. An embodiment may also include a behind the ear (BTE) processor template having a processor outline defining an area corresponding to an external BTE processor device of the bilateral hearing implant system, and configured to fit behind the ear pinna of the recipient patient at the adjustable connection with the implant stimulator template, and configured to conform against an underlying side of the patient's head.

The adjustable connection may be configured to enable the implant stimulator template to adjustably pivot through an adjustment angle with respect to the outer ear pinna. For example, the adjustable connection may be configured to allow adjustable pivoting through a limited range of recommended adjustment angles, and/or there may be an angle indicator scale configured to provide a visual indication of the adjustment angle, and/or there may be a holding magnet located within the outer outline of the implant stimulator templates configured to hold the implant stimulator template securely on the skin over an implanted magnet of a previously implanted stimulator to allow determination of the adjustment angle.

The implant stimulator template may include marking openings configured for location marking on the underlying tissue during implantation surgery. The implant stimulator template may be made of malleable plate metal and/or at least one template may be made of resilient polymer material.

DETAILED DESCRIPTION OF SPECIFIC EMBODIMENTS

Embodiments of the present invention are directed to surgical template arrangements for symmetric implantation of bilateral hearing implant systems. These are used before and/or during implantation surgery to help the surgeon to locate the implant stimulator device in symmetrical locations on both sides of the temporal bone. Such template arrangements can also be used for surgeries that require a special angle between the implant stimulator and the external BTE processor. By establishing controlled symmetric implantation sites for a bilateral hearing system, such embodiments promote optimal hearing in such systems including sound direction perception. Symmetric implantation sites are also preferred for aesthetic reasons.

Figure 1:
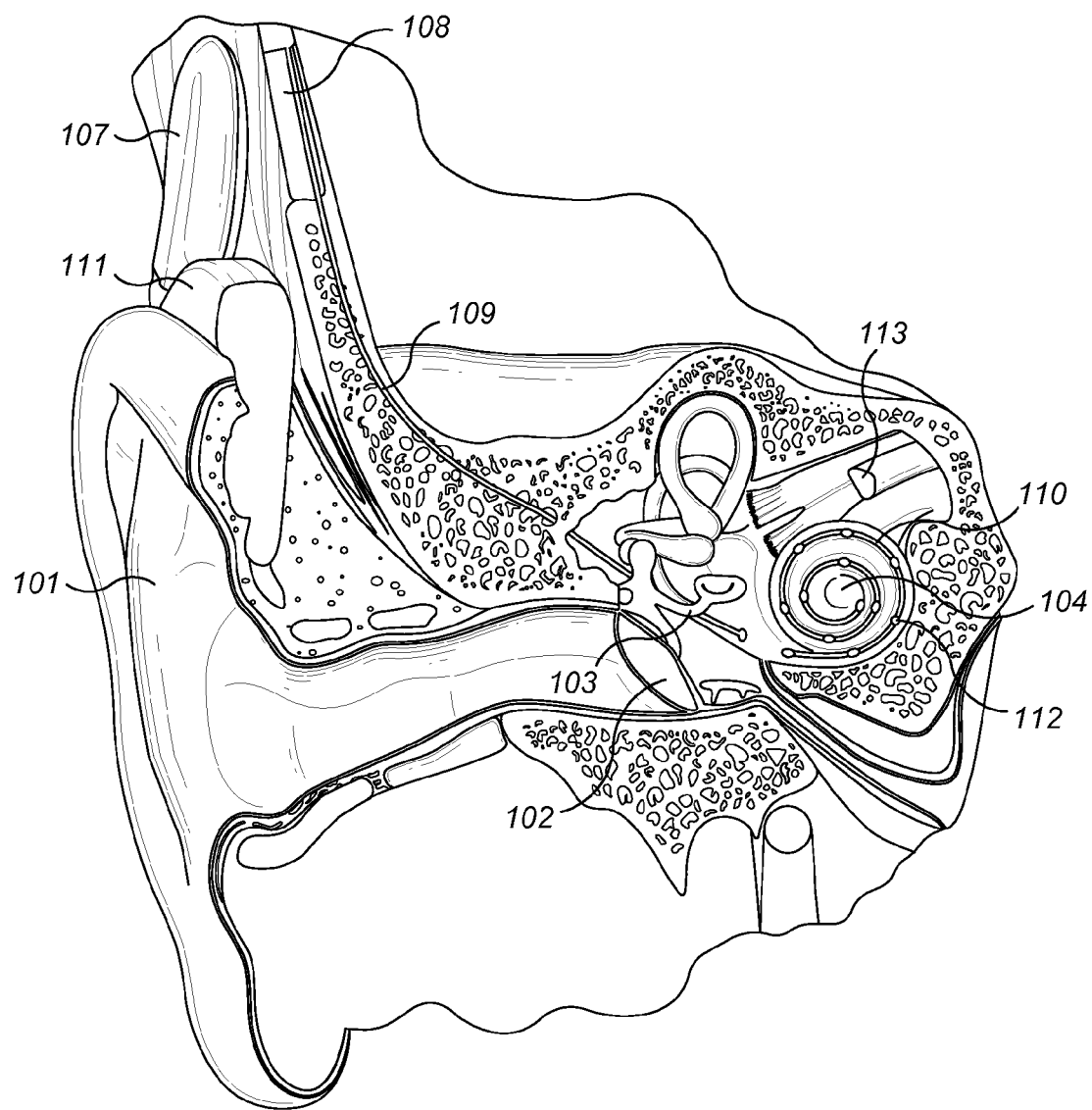
FIG. 1 shows a section view of a human ear with a typical auditory prosthesis system designed to deliver electric stimuli to the inner ear.
Figure 2B:
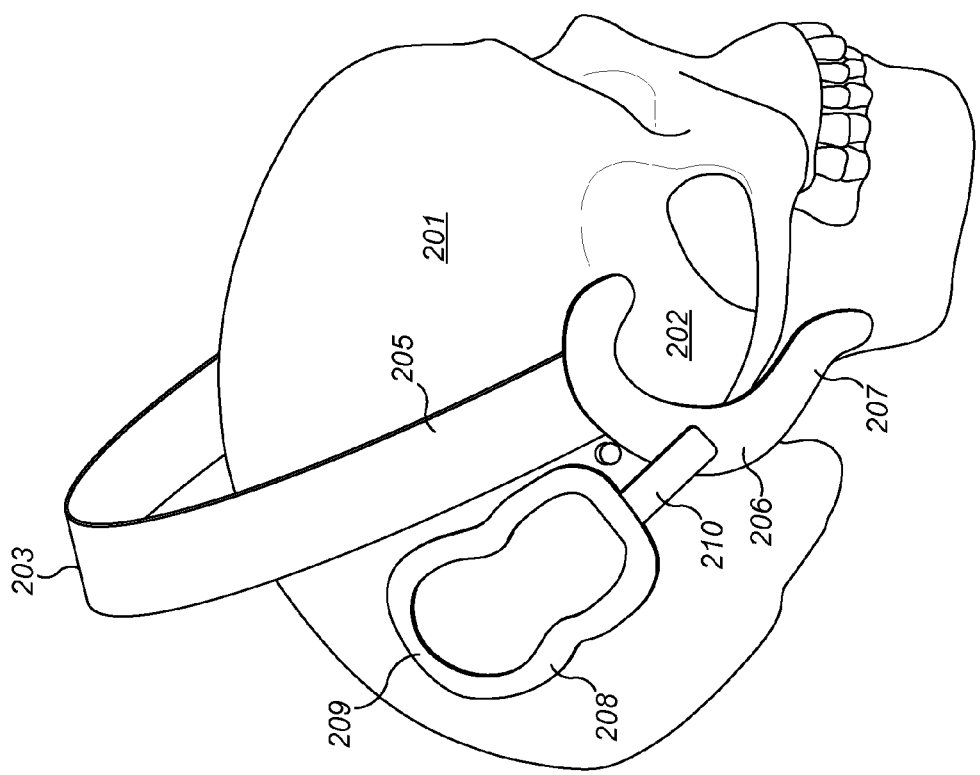
FIG. 2A-2B shows an embodiment of a symmetric surgical template arrangement for implantation of bilateral hearing implant systems based on an adjustable headpiece.
Figure 2A:
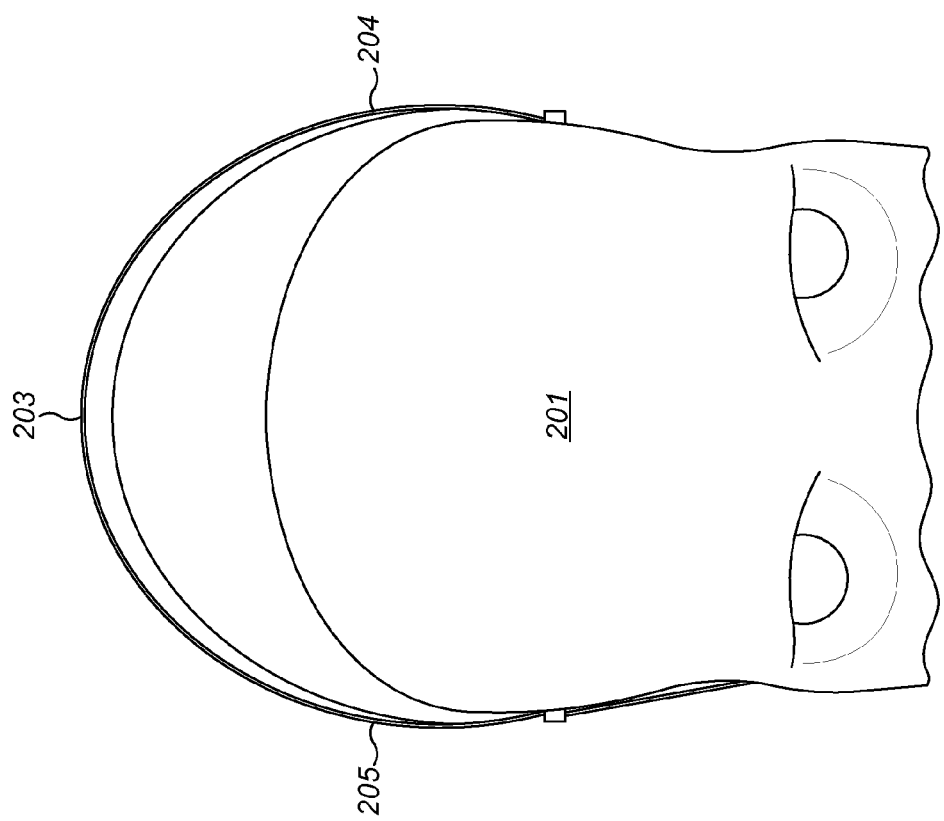

FIG. 2A-2B shows an embodiment of a symmetric surgical template arrangement for bilateral hearing implant systems that uses an adjustable headpiece 203. The adjustable headpiece 203 has left and right sides 204 and 205 respectively which are configured to fit over the patient's head 201. During implantation surgery, the headpiece 203 is first fixed to the patient's head 201 and adjusted to the size of the patient's head 201 (adults vs. children).

On each side of the adjustable headpiece 203 there are left and right behind the ear (BTE) processor templates 205 that are configured to fit behind the ear pinna 202 of the patient's head 201. Each BTE processor template 205 is adapted to conform against an underlying side of the patient's head 201, and has a processor outline 207 that defines an area corresponding to an external BTE processor device of the bilateral hearing implant system in a post-surgical operational position. There also are left and right implant stimulator templates 208, each connected to a corresponding BTE processor template 206 by an adjustable connection 209. The implant stimulator templates 208 also are configured to conform against an underlying side of the patient's head 201. Each implant stimulator template 208 has an implant outline 210 that defines an area corresponding to an implanted stimulator of the bilateral hearing implant system.

Each adjustable connection 209 is configured to allow adjustment of the position of the implant stimulator template 208 with respect to the corresponding BTE processor template 206 so as to define stimulator implantation sites at symmetric locations on each side of the patient's head 201. For example, in the embodiment shown in FIGS. 2A and 2B, each adjustable connection 209 configured to enable the corresponding implant stimulator template 208 to adjustably pivot through an adjustment angle with respect to the corresponding BTE processor template 206.

Although FIG. 2 shows an embodiment with BTE processor templates 206, in some embodiments one or both of those may be omitted. For example, in some bilateral hearing systems, there may only be one BTE processor on one side, with no BTE processor on the other side. In that case, the BTE processor template 206 is only needed and used on that side. In other systems, the BTE processor templates 206 may be omitted for other reasons. When there is no BTE processor template 206, the implant stimulator template 208 may be directly connected to the adjustable headpiece 203 by an adjustable connector 209.

Figure 3:
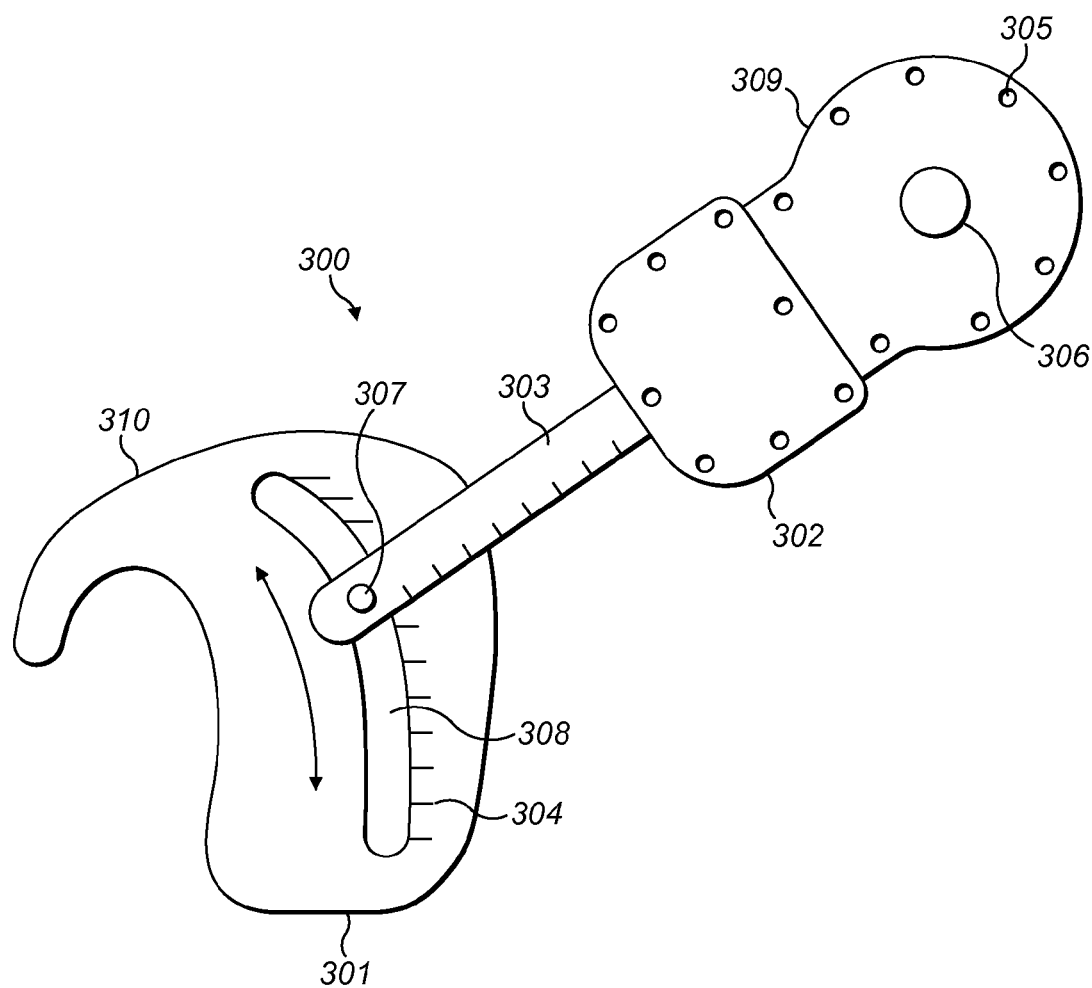
FIG. 3 shows another embodiment of a symmetric surgical template arrangement for implantation of bilateral hearing implant systems without a headpiece.

FIG. 3 shows another embodiment of another symmetric surgical template arrangement 300 without a headpiece. A behind the ear (BTE) processor template 301 is configured to fit behind the ear pinna of the recipient patient and to conform against an underlying side of the patient's head. The BTE processor template 301 also has a processor outline 310 that defines an area corresponding to an external BTE processor device of the bilateral hearing implant system in a post-surgical operational position. An implant stimulator template 302 is connected to the BTE processor template 301 by an adjustable connection 303 and also is configured to conform against an underlying side of the head. The implant stimulator template 302 has an implant outline 309 defining an area corresponding to an implanted stimulator of the bilateral hearing implant system. The adjustable connection 303 is configured to allow adjustment of the position of the implant stimulator template 302 with respect to the BTE processor template 301 so as to define stimulator implantation sites at symmetric locations on each side of the patient's head.

In the embodiment shown in FIG. 3, the adjustable connection 303 is configured to enable the implant stimulator template 302 to slide within an adjustment slot 308 about an adjustable pivot 307 to set an adjustment angle with respect to the BTE processor template 301. Here the adjustable connection 303 allows adjustable pivoting of the implant stimulator template 302 through a limited range of recommended adjustment angles as shown by an angle indicator scale 304 that provides a visual indication of the adjustment angle. In addition, the adjustable connection 303 also allows adjustment of the distance between the implant stimulator template 302 and the BTE processor template 301 as shown on an indexed scale along the length of the adjustable connection 303.

The implant stimulator template 302 also has a holding magnet 306 located within the outer outline 309 that is configured to hold the implant stimulator template 302 securely on the skin over an implanted magnet of a previously implanted stimulator to allow determination of the adjustment angle. The implant stimulator template 302 also includes marking openings 305 that are configured for location marking on the underlying tissue during implantation surgery. For example, the surgeon may use a needle and/or a syringe through the marking openings 305 to apply bone markers through the skin directly on the skull of the patient or a marker pen directly on the skin to show the desired location of the implant stimulator. Any or all of the templates may specifically be made of malleable plate metal and/or resilient polymer material.

As with the previous FIG. 2 embodiment, in some embodiments of a surgical template arrangement 300, one or both of BTE processor templates 301 may be omitted. For example, in some bilateral hearing systems, there may only be one BTE processor on one side, with no BTE processor on the other side. In that case, the BTE processor template 301 is only needed and used on that side. In other systems, the BTE processor templates 301 may be omitted for other reasons. When there is no BTE processor template 301, the implant stimulator template 302 may be configured to fit behind the ear pinna of directly by an adjustable connection 303.

Figure 4:
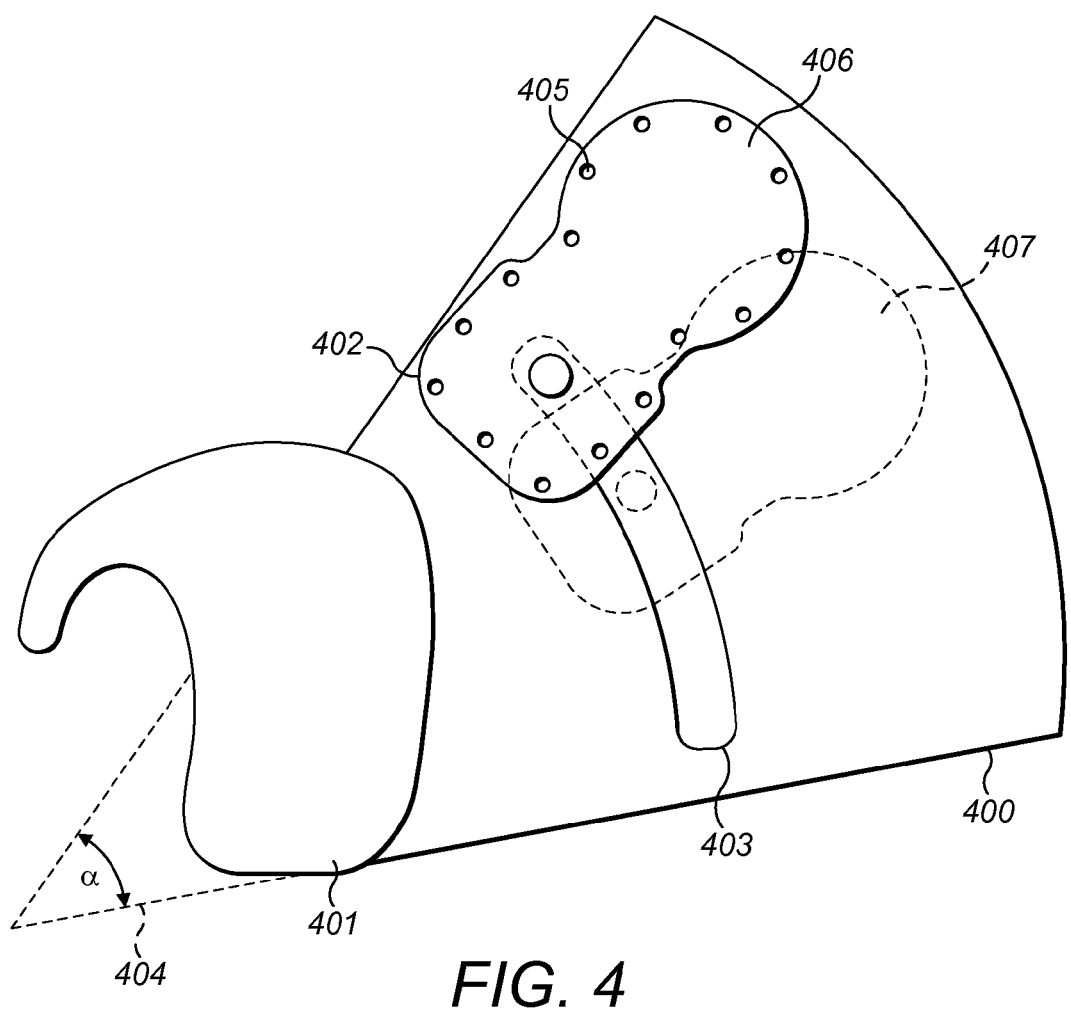
FIG. 4 shows another embodiment of a symmetric surgical template arrangement for implantation of bilateral hearing implant systems without a headpiece.

FIG. 4 shows another embodiment of a symmetric surgical template arrangement 400 with BTE processor template 401 that is connected to an implant stimulator template 405 by an adjustable malleable plate 402. An adjustable angle setting slot 403 allows setting an adjustment angle 404 within a pre-defined recommended range by an adjustment slot 403; for example as shown in FIG. 4, from a first position 406 at a first adjustment angle 404 to a second position 407 at a second adjustment angle.

Any or all of the templates and/or the adjustable connection in the above embodiments may specifically be made of malleable plate metal and/or resilient polymer material and they may be reusable or single use. For example, they may be made of thin bendable surgical grade stainless steel to be adaptable to individual head shape. And the templates and their labelling are configured for use on both sides of the head, left and right. This may include having labels and markings on both sides of the template arrangements.

Template arrangements such as those described above can be used as a planning tool on the skin of the patient before and during implantation surgery for a bilateral hearing implant system. For example, after implantation of a first implant on one side, the implant magnet of the first implant that is located under the skin can be located and used as a reference point for planning the second implant. When the implant magnet position is defined the adjustment angle between the two template parts can be measured. The same adjustment angle is then used for the opposite side of the patient's head where the second system will be implanted. The marking hole in the implant stimulator template can be used to mark the implant target location directly on the skull or on the skin of the patient.

Such template arrangements can ensure symmetrical fixation of the implant. It also reduces the surgical time in marking the implant stimulator position. Symmetrical positioning of the two implants also has a better cosmetic effect for bilateral implanted patients because of the symmetric appearance of the external parts.

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for hearing prostheses other than cochlear implants such as an auditory brainstem implant with the electrical stimuli presented by electrodes within or adjacent to the cochlear nucleus, or an auditory midbrain implant with the electrical stimuli presented by electrodes on or within the inferior colliculus. In addition, corresponding methods and systems may also be used for deep brain stimulation.

What is claimed is:

1. A symmetric surgical template arrangement for a bilateral hearing implant system, the arrangement comprising:
   an adjustable headpiece with left and right sides is configured to fit over the head of a surgical patient;
   left and right implant stimulator templates, each connected to a corresponding left and right side of the adjustable headpiece by an adjustable connection and configured to conform against an underlying side of the patient's head, wherein each implant stimulator template has an implant outline defining an area corresponding to an implanted stimulator of the bilateral hearing implant system, and wherein each adjustable connection is configured to allow adjustment of the position of the implant stimulator template with respect to the adjustable headpiece so as to define stimulator implantation sites at symmetric locations on each side of the patient's head; and
   at least one (BTE) processor template located on the adjustable headpiece at one of the adjustable connections to the corresponding left and right side implant stimulator templates, wherein the at least one BTE processor template has a processor outline defining an area corresponding to an external BTE processor device of the bilateral hearing implant system, and wherein the at least one BTE processor template is configured to fit behind the ear pinna of the recipient patient in a post-surgical operational position and conform against an underlying side of the patient's head.

2. The template arrangement according to claim 1, wherein each adjustable connection is configured to enable the corresponding implant stimulator template to adjustably pivot through an adjustment angle with respect to the adjustable headpiece.

3. The template arrangement according to claim 2, wherein each adjustable connection is configured to allow adjustable pivoting through a limited range of recommended adjustment angles.

4. The template arrangement according to claim 2, further comprising:
   an angle indicator scale configured to provide a visual indication of the adjustment angle.

5. The template arrangement according to claim 2, further comprising:
   a holding magnet located within the outer outline of one of the implant stimulator templates configured to hold that implant stimulator template securely on the skin over an implanted magnet of a previously implanted stimulator to allow determination of the adjustment angle.

6. The template arrangement according to claim 1, wherein each implant stimulator template includes a plurality of marking openings configured for location marking on the underlying tissue during implantation surgery.

7. The template arrangement according to claim 1, wherein at least one template is made of malleable plate metal.

8. The template arrangement according to claim 1, wherein at least one template is made of resilient polymer material.

9. The template arrangement according to claim 1, wherein the at least one BTE processor template comprises a pair of left and right side BTE processor templates, each BTE processor template being located on the adjustable headpiece at the adjustable connection for the corresponding left and right side implant stimulator templates.

\* \* \* \* \*